United States Patent [19]

White et al.

[11] Patent Number: 4,775,750

[45] Date of Patent: Oct. 4, 1988

[54] PROCESS FOR PREPARING SODIUM CEFUROXIME

[75] Inventors: Herbert J. White, Chalfont St. Giles; David T. Eastlick, Grange-over-Sands; John F. Oughton, Gerrards Cross, all of England

[73] Assignee: Glaxo Group Limited, London, England

[21] Appl. No.: 936,361

[22] Filed: Dec. 1, 1986

Related U.S. Application Data

[63] Continuation of Ser. No. 635,122, Jul. 27, 1984, abandoned.

[30] Foreign Application Priority Data

Jul. 29, 1983 [GB] United Kingdom ............... 8320520

[51] Int. Cl.$^4$ ........................................... C07D 501/34
[52] U.S. Cl. ................................................... 540/222
[58] Field of Search ............... 540/222, 228, 225, 227; 514/202

[56] References Cited

U.S. PATENT DOCUMENTS 4,079,179  3/1978  Christensen et al. ................. 540/30
4,298,732  11/1981  Strables ................................. 544/20

FOREIGN PATENT DOCUMENTS 2043070  10/1980  United Kingdom .

*Primary Examiner*—Nicholas S. Rizzo
*Attorney, Agent, or Firm*—Bacon & Thomas

[57] ABSTRACT

There is disclosed a process for preparing sodium cefuroxime in very high purity. The process comprises reacting (6R,7R)-7-[Z-2-(fur-2-yl)-2-methoxyimino-acetamido]-3-hydroxymethylceph-3-em-4-carboxylic acid with a halosulphonyl isocyanate in an alkyl acetate solvent, hydrolyzing the resulting intermediate product, forming sodium cefuroxime by the addition of the sodium salt of a weak acid and isolating the sodium cefuroxime in high purity. The use of methyl acetate is particularly preferred and reaction can be carried out at from −25° to +25° C. The hydrolysis, generally in situ, may be carried out at from 10° to 30° C. Fewer steps are required than in previous processes and the product is of higher purity.

8 Claims, No Drawings

PROCESS FOR PREPARING SODIUM CEFUROXIME

This application is a continuation of application Ser. No. 635,122, filed July 27, 1984, now abandoned.

This invention relates to improvements in or relating to antibiotics. More particularly it relates to improvements in a process for the preparation of sodium cefuroxime.

Cefuroxime, (6R,7R)-7-[Z-2-(fur-2-yl)-2-methoxyiminoacetamido]-3-carbamoyloxymethyl-ceph-3-em-4-carboxylic acid as described and claimed in British Patent Specification No. 1,453,049 is a valuable broad spectrum antibiotic characterised by high activity against a wide range of gram-positive and gram-negative microorganisms, this property being enhanced by the very high stability of the compound to $\beta$-lactamases produced by a range of gram-negative microorganisms.

Ceruroxime may be administered, in human or veterinary medicine, as a non-toxic derivative, i.e. one which is physiologically acceptable at the dosage at which it is administered. Such non-toxic derivatives conveniently include those salts, e.g. alkali metal, alkaline earth metal and organic base salts which on admixture with sterile, pyrogen-free water form aqueous solutions or suspensions for injection. In British Patent Specification No. 1,453,049 the sodium salt of cefuroxime is described as being a substance well suited to administration on injection and it is now recognised as being an antibiotic of outstanding value. For convenience this sodium salt will hereinafter be referred to as sodium cefuroxime.

In our British Patent Specification No. 2043070, we have described a process for the preparation of sodium cefuroxime, starting from (6R,7R)-7-[Z-2-(fur-2-yl)-2-methoxyiminoacetamido]-3-hydroxymethylceph-3-em-4-carboxylic acid, which involves reacting this compound with trichloroacetyl isocyanate, followed by treatment of the product with an alcohol and a solution of sodium 2-ethylhexanoate. Whilst this reaction does have a number of advantages over processes proposed earlier, in view of the small number of steps involved and its general simplicity, there is still a need to be able to prepare a purer product and for an even simpler or more economical process capable of providing it.

In particular, the process of Britich Patent Specification No. 2043070 requires as a specific step the addition to the product of an alcohol in the presence of a base to alcoholyse the protecting group. This creates a multi-component organic solvent system from which the sodium cefuroxime crystallises as a solvate, usually the tetrahydrofuran solvate, and this solvate has to be dried to produce the sodium cefuroxime.

We have now been able to devise a process for preparing sodium cefuroxime in a higher degree of purity and which avoids much of the complication of this earlier process. Our new process is in fact capable of providing sodium cefuroxime in a degree of purity sufficiently high as to enable it to be used directly as a starting material either in the preparation of sodium cefuroxime in a purity highly suitable as input material for making highly pure sterile commercial product, or it may be used as a starting material from which other valuable pharmaceutical products may be made in high yield and high purity. Other particularly valuable pharmaceutical products which may be prepared from the sodium cefuroxime prepared according to the invention are cefuroxime esters such as the 1-acetoxyethyl ester of cefuroxime (cefuroxime axetil). This cannot easily be achieved using the product of our British Patent Specification No. 2043070.

Accordingly, we provide a process for the preparation of sodium cefuroxime in high purity which comprises reacting (6R,7R)-7-[Z-2-(fur-2-yl)-2-methoxyimino-acetamido]-3-hydroxymethylceph-3-em-4-carboxylic acid with a halosulphonyl isocyanate in an alkyl acetate solvent, conveniently at a temperature of from $-25°$ to $+25°$ C., hydrolysing the resulting intermediate product, preferably in situ at a temperature conveniently of from $+10°$ to $+30°$ C., forming sodium cefuroxime product by the addition of the sodium salt of a weak acid and isolating sodium cefuroxime in high purity.

The alkyl acetate solvent in which the reaction with the halosulphonyl isocyanate occurs is desirably a lower (e.g. $C_{1-4}$) alkyl acetate e.g. methyl or ethyl acetate. The halosulphonyl isocyanate is desirably chlorosulphonyl isocyanate.

The reaction is preferably effected at from about $-15°$ to $-5°$ C.

The hydrolysis which forms part of the overall process will preferably be effected by adding an aqueous medium to the reaction mixture. The aqueous medium is preferably water though a mixture of water and an appropriate organic solvent, e.g. a ketone such as acetone may be employed. The aqueous medium will desirably be added rapidly to the reaction mixture. The hydrolysis will desirably be carried out at from 10° to 25° C.

The salt of a weak acid which may be used to form the sodium cefuroxime salt in the above process is desirably the sodium salt of an acid having a pKa value of more than 3.5 The salt is preferably a salt of a carboxylic acid, particularly a $C_{2-10}$ alkanoic acid, examples of such salts including sodium acetate, sodium propionate, sodium lactate and sodium 2-ethylhexanoate, the latter being especially preferred. The salt may be added to a solution of the product of hydrolysis either as a solid or as a solution in an organic solvent e.g. lower alkyl ester, alcohol or ketone, for example, methyl or ethyl acetate, ethanol or acetone; or water.

The sodium cefuroxime produced by the process of this invention is highly pure, frequently exceeding a purity level of 90% mass/mass (m/m) (uncorrected for residual solvents). Such material is extremely suitable for further processing, for example for the preparation of highly pure sterile cefuroxime or an ester of cefuroxime such as cefuroxime 1-acetoxyethyl ester (cefuroxime axetil) in a high degree of purity.

The invention will now be more particularly described in the following non-limiting Examples. All temperatures are in °C.

EXAMPLE 1

Sodium Cefuroxime

Chlorosulphonylisocyanate (226 ml) was added to a solution of triethylamine (10 ml) in methyl acetate (3.7 l). The resulting clear solution was cooled to $-15°$ and a suspension of (6R,7R)-3-hydroxymethyl-7-[Z-2-(fur-2-yl)-2-methoxyiminoacetamido]ceph-3-em-4-carboxylic acid (763 g) in methyl acetate (2.3 l), pre-cooled to $-15°$, was added over 10 minutes. The residual solid was rinsed in with methyl acetate (700 ml). The mixture was stirred at $-5°$ for 30 minutes, a clear solution being obtained after 10 minutes. Water (1.2 l) at 18° was added rapidly to the reaction mixture, the temperature rising quickly to 10° and then slowly to 17°. The mixture was stirred for 60 minutes at 15° to give a thick, white suspension. Methyl acetate (3.6 l) was added followed by a steady addition of a solution of sodium hydroxide (288 g) in water (5.2 l). This gave a clear two-phase mixture at 26° with a pH of 2.35. The layers were separated and the upper organic layer was washed with a solution of sodium chloride (600 g) in water (2 l). The two aqueous layers were washed sequentially with methyl acetate (2 l). The organic layers were bulked, stirred with Norit SX Plus charcoal (76 g) for 30 minutes and filtered through a bed of Hyflo Supercel, the bed being washed with methyl acetate (1.5 l). The filtrate and wash were combined and stirred at 20° whilst a solution of sodium 2-ethylhexanote (338 g) in a mixture of methyl acetate (2 l) and water (40 ml) was added over 20 minutes to give a white suspension with a pH of 5.5. The suspension was stirred for 10 minutes and filtered, and the cake was washed with methyl acetate (5×1 l), sucked dry, and dried at 30° in vacuo for 24 hours to give sodium cefuroxime (851.9 g); $[\alpha]_D^{20} + 60°$ (c0.5; 0.1M pH 4.5 buffer); λmax (H$_2$O) 273 nm ($E_{1\,cm}^{1\%}$ 387); impurities by hplc 2.0% m/m. Assay (hplc) 92% m/m; Water content (Karl Fischer) 2.8% m/m; Solvents (g.l.c.) 0.5% m/m.

EXAMPLE 2

Sodium Cefuroxime

Chlorosulphonyl isocyanate (39.0 ml) was added to a stirred solution of triethylamine (1.5 ml) in ethyl acetate (280 ml) pre-cooled to −10°, the temperature of the mixture rising to 0°. This mixture was recooled to −10°, and a suspension of (6R,7R)-3-hydroxymethyl-7-[Z-2-(fur-2-yl)-2-methoxyiminoacetamido]ceph-3-em-4-carboxylic acid (114.4 g) in ethyl acetate (350 ml), pre-cooled to −12°, was blown in by nitrogen pressure. Ethyl acetate (60 ml) was used to wash through the residual solid. The temperature of the reaction mixture rose to 0°. The mixture was stirred at 0° to 3° for 40 minutes to give a clear solution which was blown under nitrogen pressure over 2½ minutes into a stirred mixture of water (180 ml) and acetone (300 ml) pre-cooled to 8°. Ethyl acetate (60 ml) was used as a line wash. The temperature of the mixture rose gradually to 25° and a granular off-white precipitate formed after ca 10 minutes. Stirring was continued for a total of 60 minutes before acetone (450 ml) was added followed by, over 5 minutes, a solution, pre-cooled to 5°, of sodium hydroxide (48 g) in water (300 ml). This gave a clear two-phase mixture at 29° with a pH of 2.2. The layers were separated and the upper, organic layer was washed with a solution of sodium chloride (90 g) in water (300 ml). The two aqueous layers were suquentially back extracted with the same portion of ethyl acetate (150 ml). The organic layers were combined and stirred with SS 110 charcoal (11.5 g) for 1 hour. The charcoal was removed by filtration on a bed of Hyflo Supercel which was washed with a mixture of acetone (150 ml) and ethyl acetate (150 ml) applied in two parts, the filtrate and wash being combined. Sodium 2-ethylhexanoate (54.9 g) was dissolved in a mixture of acetone (300 ml) and water (3 ml) and the solution was clarified by filtration through a bed of Hyflo Supercel which was washed with acetone (150 ml). The combined wash and filtrate was added over 25 minutes to the stirred cefuroxime solution to give a suspension with a pH of 6.3. The suspension was stirred for 10 minutes and filtered, and the cake was washed by displacement with acetone (4×150 ml), sucked dry for 10 minutes and dried in vacuo at 20° to give sodium cefuroxime (130.25 g); $[\alpha]_D^{20} + 60°$ (c 0.5; 0.1M pH 4.5 buffer); λmax (H$_2$O) 273 nm, ($E_{1\,cm}^{1\%}$ 382); impurities by hplc 1.8% m/m. Assay (hplc) 92% m/m; water (Karl Fischer) 2.6% m/m; solvents (g.l.c.) 0.75% m/m.

We claim:

1. A process for the preparation of sodium cefuroxime which comprises reacting (6R,7R)-7-[Z-2-(fur-2-yl)-2-methoxyimino-acetamido]-3-hydroxymethylceph-3-em-4-carboxylic acid with a halosulphonyl isocyanate in an alkyl acetate solvent, hydrolysing the resulting intermediate product, forming sodium cefuroxime by the addition of the sodium salt of a week acid and isolating the sodium cefuroxime in high purity.

2. The process of in claim 1 wherein the hydrolysis is carried out in situ.

3. The process of claim 1 wherein the alkyl acetate solvent is methyl acetate or ethyl acetate.

4. The process of claim 1 wherein the halosulphonyl isocyanate is chlorosulphonyl isocyanate.

5. The process of claim 1 wherein the reaction of (6R,7R)-7-[Z-2-(fur-2-yl)-2-methoxyimino-acetamido]-3-hydroxymethylceph-3-em-4-carboxylic acid with the halosulphonyl isocyanate is carried out at a temperature of from −25° C. to 25° C.

6. The process of claim 1 wherein the hydrolysis of the intermediate product is carried out at a temperature of from +10° to +30° C.

7. The process of claim 1 wherein the hydrolysis of the intermediate product is carried out in water or a mixture of water and a ketone.

8. The process of claim 1 wherein the salt of the weak acid used to form the sodium cefuroxime salt is the salt of an alkanoic acid having from 2 to 10 carbon atoms.

* * * * *